(12) United States Patent
Bhuyan et al.

(10) Patent No.: US 11,962,626 B2
(45) Date of Patent: Apr. 16, 2024

(54) VIDEO CONFERENCE MANAGER

(71) Applicant: ARRIS Enterprises LLC, Suwanee, GA (US)

(72) Inventors: Sudeepta Bhuyan, Karnataka (IN); Anand Madhav Rao Hallur, Karnataka (IN)

(73) Assignee: ARRIS ENTERPRISES LLC, Horsham, PA (US)

(*) Notice: Subject to any disclaimer, the term of this patent is extended or adjusted under 35 U.S.C. 154(b) by 1 day.

(21) Appl. No.: 17/896,304

(22) Filed: Aug. 26, 2022

(65) Prior Publication Data
US 2023/0071282 A1 Mar. 9, 2023

Related U.S. Application Data

(60) Provisional application No. 63/242,130, filed on Sep. 9, 2021.

(51) Int. Cl.
*H04L 65/1069* (2022.01)

(52) U.S. Cl.
CPC ................ *H04L 65/1069* (2013.01)

(58) Field of Classification Search
CPC ...... H04L 65/1066–1069; H04L 51/00–51/07; H04L 12/1813–12/1845
See application file for complete search history.

(56) References Cited

U.S. PATENT DOCUMENTS

| | | | |
|---|---|---|---|
| 9,049,262 B2 * | 6/2015 | Massover | H04L 67/63 |
| 10,200,653 B2 * | 2/2019 | Peled | H04L 65/403 |
| 10,742,817 B1 | 8/2020 | White et al. | |
| 11,197,145 B2 * | 12/2021 | Martin | H04L 67/52 |
| 2010/0088414 A1 * | 4/2010 | Lin | H04L 12/1818 709/227 |
| 2014/0354765 A1 * | 12/2014 | Yi | H04M 3/567 348/14.09 |
| 2020/0244605 A1 | 7/2020 | Nagaraja et al. | |
| 2021/0152616 A1 * | 5/2021 | Huang | H04L 65/403 |

OTHER PUBLICATIONS

International Search Report and the Written Opinion of the International Searching Authority dated Oct. 28, 2022 in International (PCT) Application No. PCT/US2022/041640.

* cited by examiner

*Primary Examiner* — Clayton R Williams
(74) *Attorney, Agent, or Firm* — Wenderoth, Lind & Ponack, L.L.P.

(57) ABSTRACT

A digital conference system can include a digital conference manager that automatically selects a digital conference service based on one or more digital conference parameters. A digital conference agent can request a digital conference configuration from a policy manager 204 that is based on the one or more digital conference parameters. The policy manager 204 can send the selected digital conference configuration to the digital conference agent that sends the selected digital conference configuration or an identifier associated with a digital conference service associated with the digital conference configuration to a digital conference service manager. The digital conference service manager establishes a digital conference connection based on the digital conference service received from the digital conference agent. The digital conference service is automatically selected without requiring extensive knowledge by the user so as to provide a customized and enhanced digital conference without burdening the user.

20 Claims, 4 Drawing Sheets

FIG. 4

VIDEO CONFERENCE MANAGER

BACKGROUND

Digital conferencing services or solutions (collectively referred to as digital conference services) are widely used for personal, work, and/or official related communications. The marketplace for digital conference services is crowded with each of the digital conference services providing various features to users. However, as the digital conferencing solutions become more distinct and as users are required to utilize more than one digital conference services, a decision as to which digital conference service to use for a particular communication has become increasing more complicated and cumbersome for a user. Thus, there is a need for a system to manage the various digital conference services available for use by a user so as to maximize the services provided by each respective digital conference service while providing an improved experience for a user.

SUMMARY

Digital conference services are becoming ubiquitous with network environments, including network environments associated with any of a home network, an enterprise network, a public network, or any other type of network that allows for digital communications. A variety of service providers for one or more digital conference services have arisen with each digital conference service providing one or more features. These one or more features can include, but are not limited to, any of one or more digital call management techniques, one or more compression techniques, one or more types of billing plans or one or more service charges, a communications service as a platform (CPaaS), one or more value-added services, any other service or feature particular to the digital conference solution, and any combination thereof. The one or more features can become overwhelming for a user such that a user finds it difficult to select an appropriate digital conference service for a particular event. For example, a doctor may have a scheduled appointment, a digital conference, with a patient that requires a certain level of security or privacy but without knowing each feature provided by each digital conference service the doctor may be overwhelmed with the decision of which digital conference service provides the appropriate one or more features for the scheduled appointment. Thus, there is a need to provide a digital conference manager that can determine the appropriate digital conference service based on any one or more factors including, but not limited to, any of a caller, a callee, a type of digital conference, one or more network parameters, any other digital conference factor, or any combination thereof.

According to aspects of the present disclosure there are provided novel solutions for a digital conference system. The digital conference system can include a digital conference manager for automatically selecting a digital conference service for a particular user, a digital conference, and/or a participant. The digital conference system can include a policy manager, a digital conference agent and a digital conference service manager so as to provide a user with an improved digital conference service that best fits the needs or other network parameters associated with the requested digital conference. The digital conference manager can determine the appropriate digital conference service and configuration for a scheduled digital conference automatically such that the user (the caller and/or the callee) are not required to understand, be aware of, and/or affirmatively select any particular setting for the digital conference. In this way, the user is provided with an improved digital conference service.

An aspect of the present disclosure provides a digital conference system to establish a digital conference connection. The digital conference system comprises a memory storing one or more computer-readable instructions and a processor. The processor is configured to execute the one or more computer-readable instructions to perform one or more operations to receive a digital conference request for a digital conference connection, determine one or more digital conference parameters based on the digital conference request, select a digital conference configuration from a plurality of digital conference configurations based on the one or more digital conference parameters, select a digital conference service from a plurality of digital conference services based on the digital conference configuration, and establish the digital conference connection using the digital conference service.

In an aspect of the present disclosure, the plurality of digital conference services comprises a health information portability and applicability act (HIPAA) service, an enterprise service, and a basic service.

In an aspect of the present disclosure, each of the plurality of digital conference configurations are associated with a user profile, a participant profile, or both.

In an aspect of the present disclosure, the digital conference configuration is selected based on the user profile, the participant profile, or both.

In an aspect of the present disclosure, the plurality of digital conference configurations comprise at least one of a network configuration, an entitlement configuration, a contact management configuration, and a quality configuration.

In an aspect of the present disclosure, the at least one of the plurality of digital conference services comprises a calling software development kit (SDK).

In an aspect of the present disclosure, the processor is further configured to execute the one or more computer-readable instructions to perform one or more further operations receive a user input from a user interface, and wherein the one or more digital conference parameters comprises the user input.

An aspect of the present disclosure provides a method for a digital conference manager to establish a digital conference connection. The method comprising receiving a digital conference request for a digital conference connection, determining one or more digital conference parameters based on the digital conference request, selecting a digital conference configuration from a plurality of digital conference configurations based on the one or more digital conference parameters, selecting a digital conference service from a plurality of digital conference services based on the digital conference configuration, and establishing the digital conference connection using the digital conference service.

In an aspect of the present disclosure, the method is such that the plurality of digital conference services comprises a health information portability and applicability act (HIPAA) service, an enterprise service, and a basic service.

In an aspect of the present disclosure, the method is such that each of the plurality of digital conference configurations are associated with a user profile, a participant profile, or both.

In an aspect of the present disclosure, the method is such that the digital conference configuration is selected based on the user profile, the participant profile, or both.

In an aspect of the present disclosure, the method is such that the plurality of digital conference configurations comprise at least one of a network configuration, an entitlement configuration, a contact management configuration, and a quality configuration.

In an aspect of the present disclosure, the method is such that the at least one of the plurality of digital conference services comprises a calling software development kit (SDK).

In an aspect of the present disclosure, the method further comprises receiving a user input from a user interface and wherein the one or more digital conference parameters comprises the user input.

An aspect of the present disclosure provides a non-transitory computer-readable medium of a digital conference system storing one or more computer-readable instructions for establishing a digital conference connection. The one or more computer-readable instructions when executed by a processor of the digital conference system, cause a digital conference manager of the digital conference system to perform one or more operations including the steps of the methods described above.

The above-described novel solution may be implemented at a digital conference system that includes one or more devices, one or more software applications or both for automatically selecting a digital conference service for a digital conference based on one or more digital conference parameters. Thus, according to various aspects of the present disclosure described herein, it is possible to automatically establish a digital conference connection that utilizes a digital conference service that best suits the needs, requirements, or preferences of a particular user and/or is customized for a particular participant, network, or environment so as to provide an improved digital conference connection.

BRIEF DESCRIPTION OF DRAWINGS

In the drawings, like reference numbers generally indicate identical, functionally similar, and/or structurally similar elements.

DETAILED DESCRIPTION

The following detailed description is made with reference to the accompanying drawings and is provided to assist in a comprehensive understanding of various example embodiments of the present disclosure. The following description includes various details to assist in that understanding, but these are to be regarded merely as examples and not for the purpose of limiting the present disclosure as defined by the appended claims and their equivalents. The words and phrases used in the following description are merely used to enable a clear and consistent understanding of the present disclosure. In addition, descriptions of well-known structures, functions, and configurations may have been omitted for clarity and conciseness. Those of ordinary skill in the art will recognize that various changes and modifications of the examples described herein can be made without departing from the spirit and scope of the present disclosure.

Figure 1:
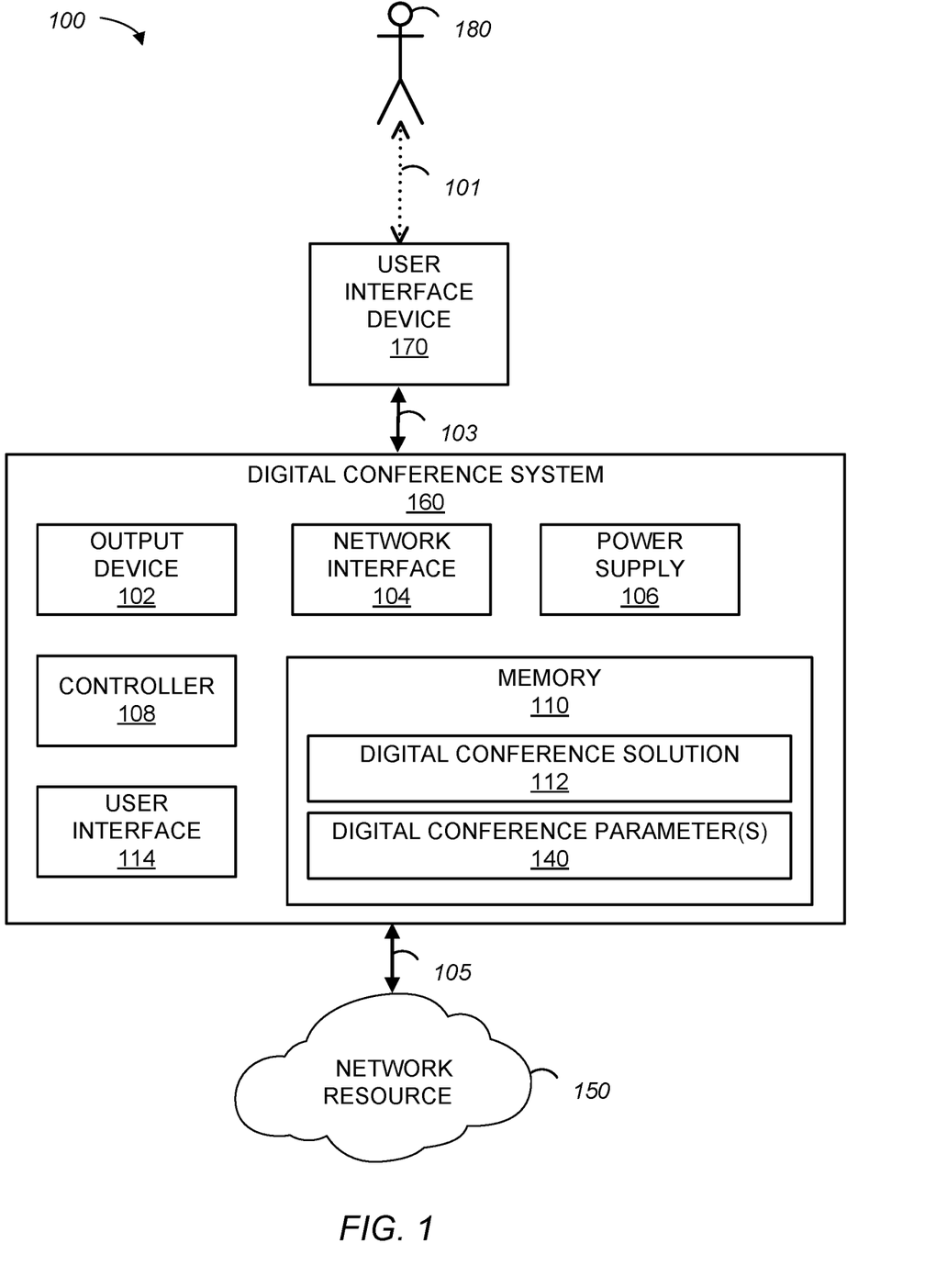
FIG. 1 is a block diagram of a digital conference system, according to one or more aspects of the present disclosure.

FIG. 1 is a block diagram of a digital conference environment 100, according to one or more aspects of the present disclosure. It should be appreciated that various example embodiments of inventive concepts disclosed herein are not limited to specific numbers or combinations of devices, and there may be one or multiple devices and/or components in the digital conference environment 100, which may itself consist of multiple communication networks and various known or future developed wireless connectivity technologies, protocols, devices, and the like.

The digital conference environment 100 can comprise a network resource 150, a digital conference system 160, a user interface device 170 and a user 180. The digital conference system 160 can comprise an output device 102, a user interface 114, a controller 108, a network interface 104, a power supply 106 and a memory 110. The digital conference system 160 can be connected to the network resource 150 via a connection 105 and a user interface device or user input device 170 via a connection 103. The digital conference system 160 can be any of a set-top box, a centralized device, a computing system, such as a computer, a laptop, a table, an enterprise system, such as a server, a mobile telephone, a personal digital assistant, any other device and/or system for receiving, processing, and/or otherwise analyzing one or more inputs or commands from one or more user interface device or user input device 170, establishing a digital conference connection, or both, or any combination thereof. A digital conference connection can comprise a connection that facilitates or enables a digital conference, such as a video conference, an audio conference, a text-based conference, or any combination thereof.

A user, such as a user 180, can be a user, a host or an initiator (such as a caller or requestor associated with a digital conference), a participant (such as a callee or the recipient of a request for a digital conference), an electronic system capable of setting, scheduling, requesting or otherwise participating in a digital conference, or any combination thereof. The user 180 can provide one or more commands via a connection 101 to the digital conference system 160 to establish a digital conference connection, to set up a digital conference connection, or any other command related to a digital conference between any one or more users, such as a user or host and a participant or a caller and a callee. The digital conference system 160 can receive one or more commands from the one or more commands via the connection 103. The one or more commands can comprise any of an instruction, a request, any other command, or any combination thereof associated with a digital conference, such as configuring, setting, establishing, or otherwise providing a digital conference connection.

The network resource 150 can comprise a server, an information handling system, one or more applications, software, one or more websites and/or uniform resource locator (URL), software as a system (SAAS), an Internet service provider (ISP) a cloud management system, a cloud controller, a network monitoring system, a network reporting and analytics system, a secure network access system, an original equipment manufacturer (OEM) network resource or cloud, any other network management and/or control system, any other type of hardware and/or software for establishing a digital conference connection between the digital conference system 160 and any other computing device or system, for example, a digital conference between a plurality of users. The network resource 150 can comprise a repository for storing any one or more digital conference parameters or any other information associated with a digital conference connection. The network resource 150 can be connected to the digital conference system 160 via a connection 105, such as a cloud services connection.

The output device 102 can comprise any device that provides for the playback and/or reproduction of any of audio, video, multimedia content, any other content, or any combination thereof, for example, to a user 180 within proximity 101 including, but not limited to, any of a speaker, a sound bar, a display (such as a television, a monitor, a projector, and/or any other audio playback device, video playback device, or both), any other device that is capable of providing multi-media content, such as a digital conference, for consumption by a user 180, or any combination thereof. For example, output device 102 can provide a display for a video conference between user 180 and any other one or more participants. In one or more embodiments, the output device 102 is a separate device connected to the digital conference system 160.

The network interface 104 can include, but is not limited to, various network cards, interfaces, and circuitry implemented in software and/or hardware to enable communications with any of one or more elements of user interface device 170, network resource 150, any other device, or a combination thereof using the communication protocol(s) in accordance with any connection, for example, connection 103 and 105. The power supply 106 supplies power to any one or more of the internal elements of the multimodal authentication device 160, for example, through an internal bus. The power supply 106 can be a self-contained power source such as a battery pack with an interface to be powered through an electrical charger connected to an outlet (for example, either directly or by way of another device). The power supply 106 can also include a rechargeable battery that can be detached allowing for replacement such as a nickel-cadmium (NiCd), nickel metal hydride (NiMH), a lithium-ion (Li-ion), or a lithium Polymer (Li-pol) battery.

The controller 108 controls the general operations of the digital conference system 160 and can comprise any of or any combination of a central processing unit (CPU), a hardware microprocessor, a hardware processor, a multi-core processor, a single core processor, a field programmable gate array (FPGA), a microcontroller, an application specific integrated circuit (ASIC), a digital signal processor (DSP), or other similar processing device capable of executing any type of computer-readable instructions, algorithms, or software including the digital conference solution or software 112 stored in memory 110 for controlling the operation and functions of the digital conference system 160 in accordance with the embodiments described in the present disclosure. Communication between any of the element (for example, elements 102, 104, 106, 108, 110, and/or 114) of the digital conference system 160 can be established using an internal bus.

The memory 110 can comprise a single memory or one or more memories or memory locations that can include, but are not limited to, any of a random access memory (RAM), a dynamic random access memory (DRAM) a memory buffer, a hard drive, a database, an erasable programmable read only memory (EPROM), an electrically erasable programmable read only memory (EEPROM), a read only memory (ROM), a flash memory, logic blocks of a field programmable gate array (FPGA), an optical drive, a hard disk or any other various layers of memory hierarchy. The memory 110 can be used to store any type of computer-readable instructions, software, or algorithms including software or digital conference solution 112 for controlling the general function and operations of the multimodal authentication device 160 in accordance with the embodiments described in the present disclosure. In one or more embodiments, software or digital conference solution 112 includes one or more applications, one or more computer-readable instructions, one or more elements or components, one or more modules, or any combination thereof for providing or establishing a digital conference connection. The memory 110 can store one or more digital conference parameters 140. The one or more digital conference parameters can comprise any of a user input or command received from a user interface 114 (for example, via a user interface device 170), one or more profiles (such as one or more profiles associated with a user (such as a user profile, including a profile associated with user 180 or the user the digital conference is directed to) or any other user including, but not limited to, any of a host (such as a host profile), a participant (such as a participant profile), a requestor (a requestor profile), a receiver (a receiver profile), a caller (such as a caller profile), a callee (such as a callee profile), or any combination thereof), one or more network parameters (such as any of bandwidth, throughput, network usage, data plan, speed, efficiency, a network identifier, for example, an identifier indicative of a network associated with any user, one or more digital conference services, an ISP, any other entity, system, or user, or any combination thereof), any other network parameter (for example, a security level of the network, such as an open network a public network, an unencrypted network, a closed network, an encrypted network (Wi-Fi protected access (WPA) including, but not limited to, WPA2 or WPA3), a password-protected network, or any combination thereof), a user identifier associated with the user 180 requesting the video conference, a network identifier associated with the network, a participant identifier associated with a user or an entity for which a digital conference is requested or directed to, a default or preferred digital conference service identifier associated with a digital conference service 207, a default or preferred digital conference service identifier associated with a digital conference service 207, a requested date and/or time for a requested digital conference, a requested length or duration of a requested digital conference, any other digital conference information, or any combination thereof.

The user interface 114 can comprise any of one or more tactile inputs (for example, a push button, a selector, a dial, a remote control unit (RCU), etc.), a camera, a keyboard, an audio input, for example, a microphone, a keypad, a liquid crystal display (LCD), a thin film transistor (TFT), a light-emitting diode (LED), a high definition (HD) or other similar display device including a display device having touch screen capabilities so as to allow interaction between one or more users 180 and the digital conference system 160, or a combination thereof.

In one or more embodiments, the digital conference system 160 is coupled or connected to a user interface device 170 via a connection 103 so as to provide and/or receive audio and/or visual inputs and/or outputs to and/or from a user 180 within a proximity 101. In one or more embodiments, the user interface device 170 or one or more elements of the user interface device 170 are incorporated within or as part of the digital conference system 160. In one or more embodiments, the user interface device 170, the output device 102, or both comprises a an audio input device (for example, a device that can receive and/or record audio or sound, such as a microphone), an audio output device (for example, a device that can output and/or record audio or sound, such as a speaker), an image capture device (for example, a device that can receive and/or record an image, including audio, video, or both, such as a camera, a recorder, a video camera, etc.), a display device (for example, a device that can output an image, such as a monitor, a display, a screen, etc.), any other element or device that provides for a video conference, or any combination thereof.

In one or more embodiments any of connection 103 or connection 105 can be a bidirectional communication link such that any one or more communications or messages can be sent and/or received by any of the digital conference system 160, the network resource 150, the user interface device 170, or any combination thereof. A connection 103 or a connection 105 can be a wired and/or wireless connection.

Figure 2:
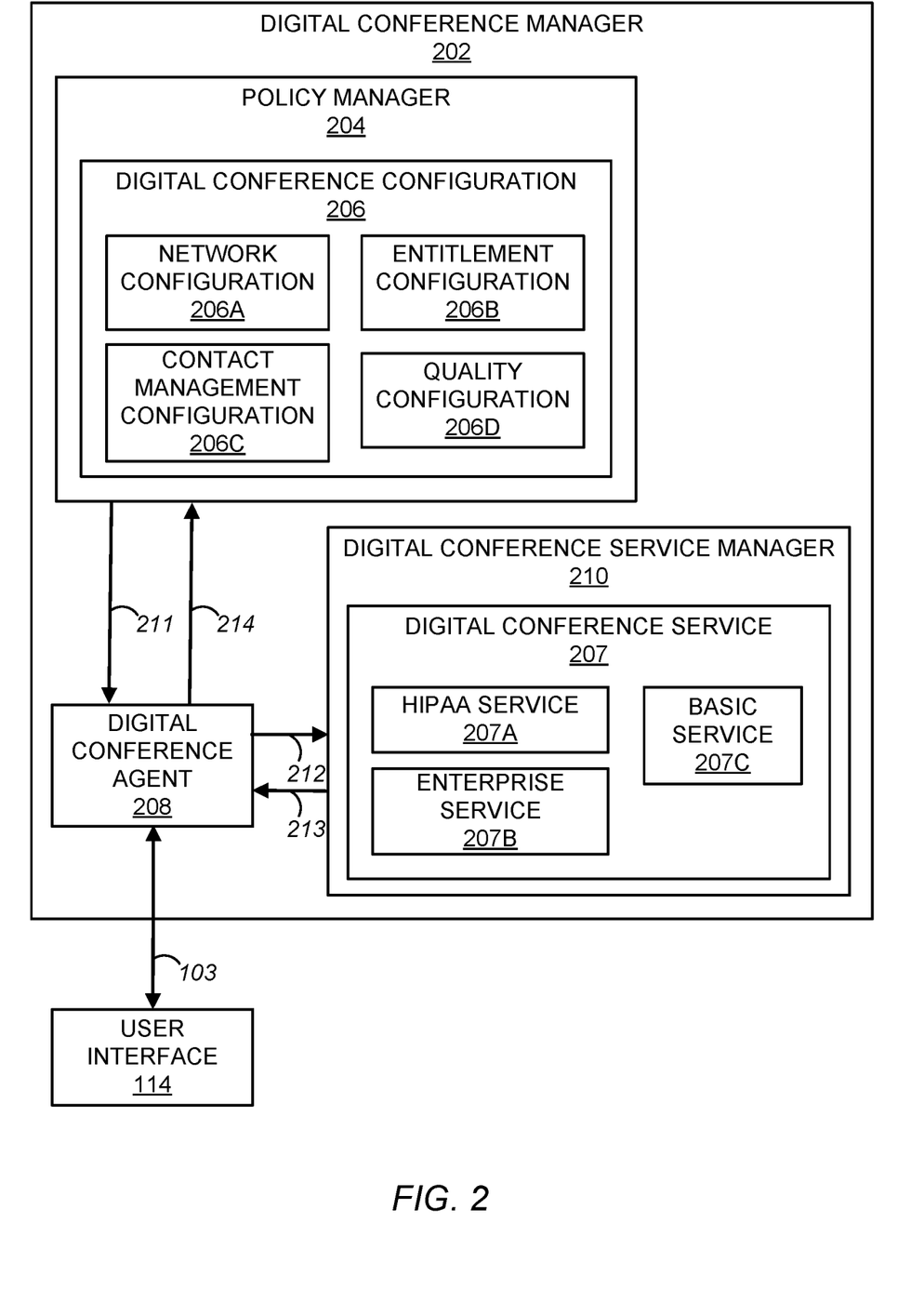
FIG. 2 is a block diagram of a digital conference manager, according to one or more aspects of the present disclosure.

FIG. 2 is a block diagram of a digital conference manager 202, according to one or more aspects of the present disclosure. In one or more embodiments, the digital conference manager 202 can be part of a digital conference solution 112, a distinct application, software, and/or one or more computer-readable instructions stored in the memory 110, a separate element, component, or module, an external element, component or module, or any combination thereof. The digital conference manager 202 can comprise a policy manager 204, a digital conference agent 208, and a digital conference service manager 210.

The digital conference agent 208 can be communicatively coupled to the digital conference configuration 206 and the digital conference service manager 210 via bi-directional connections 210 and 212, respectively. The digital conference agent 208 can receive an input or a command (a user input or command), for example, a command to initiate, set or otherwise establish a digital conference connection, from a user interface 114 via a connection 103, user interface 114, or both. The digital conference agent 208 can store the input or command received from the user interface 114 in a memory 110, a network resource 150, or both. The digital conference agent 208 determines a digital conference service 207 to use for establishing the digital conference requested by the input or command based on one or more digital conference parameters 140. The one or more digital conference parameters 140 can be associated with a particular user (such as user 180 or the intended recipient of the digital conference), the digital conference system 160, a digital conference configuration 206, a digital conference service 207, any other digital conference parameter 140, or any combination thereof. The digital conference agent 208 can obtain the one or more digital conference parameters 140 from any of a query to a network resource 150, from memory 110, from the digital conference agent 208, or any combination thereof. In one or more embodiments, the digital conference agent 208 can receive from the policy manager 204 a plurality of digital conference configurations 206 based on the one or more digital conference service parameters 140. For example, the user input or command from the user interface 114 can be indicative of any of a preference for a particular digital conference service 207, a setting or value for one or more digital conference parameters, an identifier associated with the user and/or the participant or the intended recipient of the digital conference, any other information, or any combination thereof. The digital conference agent 208 can then determine or select one or more digital conference parameters 140 associated with the digital conference request from the user interface 114. The digital conference agent 208 can send the one or more digital conference parameters 140 to a policy manager 204 that selects one or more digital conference configurations 206. The digital conference agent 208 can select a digital conference service 207 based on the one or more digital conference configurations 206, a user input, one or more digital conference service parameters 140, other information (such as a threshold value) or can send the one or more digital conference configurations 206 to the digital conference service manager 210 for the digital conference service manager 210 to select to the digital conference service 207. The digital conference service 207 can be selected based on the one or more digital conference configurations 206, one or more digital conference parameters 140 (including, but not limited to, one or more network parameters), any one or more thresholds (for example, any one or more thresholds associated with a digital conference service 207, a digital conference configuration 206, a digital conference parameter 140, or any combination thereof), or any combination thereof.

The policy manager 204 can comprise one or more digital conference configurations 206, such as any of a network configuration 206A, a contact management configuration 206C, an entitlement configuration 206B, a quality configuration 206D, or any combination thereof (collectively referred to as one or more digital conference configurations 206). The digital conference agent 208 can send a digital conference configuration request 214 to the policy manager 204 for a digital conference configuration 206. The digital conference configuration request 214 can be associated with or comprise one or more digital conference parameters 140. For example, any one or more digital conference configurations 206 can be associated with a user profile. The policy manager 204 can query which of the plurality of digital conference configurations 206 are associated with the user profile and select a digital conference configuration 206 from the results of the query, for example, based on one or more digital conference parameters 140. The policy manager 204 can select a digital conference configuration 206 based on the digital conference configuration request 214, such as based on a user input, a comparison of any one or more of the digital conference parameters 140 to one or more associated thresholds associated, one or more user settings, one or more network conditions, a history or log of one or more digital conferences, or any combination thereof. For example, the digital conference agent 208 can send information to the policy manager 204 in a digital conference configuration request that comprises the user input or command, the one or more digital conference parameters 140, or both. The policy manager 204 uses this information to select a digital conference configuration 206. The policy manager 204 can send a digital conference configuration response 211 to the digital conference agent 208 that comprises a digital conference configuration 206 selected by the policy manager 204 based on the one or more digital conference parameters 140. In one or more embodiments, the digital conference parameters 140 are determined in real-time as opposed to being retrieved from a memory 110 or a network resource 150.

The network configuration 206A can comprise one or more network identifiers that correspond to one or more networks that can be used to facilitate the requested digital conference based on any of the one or more digital conference parameters 140 or one or more network parameters available to the digital conference system. In one or more embodiments, the one or more digital conference parameters 140 can include the one or more network parameters and the one or more network parameters can be updated periodically, routinely, or on-demand. For example, if the digital conference system 160 associated with the user 180 seeking to initiate or setup a digital conference is connected to an open Wi-Fi or network that does not meet a security level criteria, then the policy manager 204 can select a network configuration 206A that indicates a digital conference service 207 with a security level that meets the security level criteria, such as a HIPAA service 207A or an enterprise service 207B.

The entitlement configuration 206B can comprise one or more levels of service associated with the user 180, the digital conference system 160, the participant, or any combination thereof. For example, if the user 180 is associated with a premium or high tier paid service then the policy manager 204 can select an entitlement configuration 206B that indicates a digital conference service 207 that indicates a high level security, an enhanced or higher resolution video quality, unlimited conference duration, or any combination thereof, such as an enterprise service 207B. As another example, if the user 180 is associated with a basic or low tier service (such as a free service) then the policy manager 204 can select an entitlement configuration 206B that indicates a basic service 207C.

The contact management configuration 206C can comprise one or more digital conference services 207 associated with a particular contact of the user 180. The contact or information associated with the contact, such as a contact profile, can be stored in a memory 110, a network resource 150, any other memory or resource, or any combination thereof. For example, the policy manager 204 can determine if a contact is associated with a particular type of digital conference service and select a contact management configuration 206C that corresponds to the particular type of digital conference service. As an example, if the user 180 requests a digital conference with a participant and the participant is associated with a contact of the user 180 that is designated as a medical professional, the policy manager 204 can select a contact management configuration 206C that corresponds to a medical professional, such as a HIPAA service 207A. As another example, if the contact is designated as a colleague or professional contact then the policy manager 204 can select a contact management configuration 206C that indicates an enterprise grade or level of security and/or quality, such as enterprise service 207B. As another example, if the contact is designated as a friend then the policy manager 204 can select a contact management configuration 206C that indicates a low quality or basic service, such as basic service 207C. In one or more embodiments, the policy manager 204 can select a contact management configuration 206C based on a user identifier, a participant identifier, or both included in the digital conference configuration request 210.

The quality configuration 206D can comprise one or more digital conference services 207 associated with a particular quality level. For example, for a digital conference associated with a medical professional and/or medical service, an enterprise call, any other digital conference where quality of the video and/or audio is important, or any combination thereof, the policy manager 206 can select a quality configuration 206D that is associated with a service that provides high or enhanced quality, high or enhanced resolution, or both, such as an enterprise service 207B and/or a HIPAA service 207A. As another example, if the network associated with the user 180 is a mobile data network then the policy manager 204 can select a quality configuration 206D that indicates a digital conference service 207 associated with low bandwidth requirements.

The digital conference agent 208 can send a digital conference service request 212 to the digital conference service manager 210 so as to initiate a digital conference and/or establish a digital conference connection based on the digital conference service request 212. The digital conference service request 212 can comprise a digital conference configuration 206 selected by the policy manager 204 based on the one or more digital conference service parameters 140 and received by the digital conference agent 208 from the policy manager 204, a digital conference service identifier that is associated with one or more digital conference services 207 of a digital conference configuration 206 selected by the policy manager 204, or both. The digital conference service manager 210 can manage one or more digital conference services 207 so as to establish a digital conference connection. In one or more embodiments, the digital conference service 207 is a software developer kit (SDK). The one or more digital conference services 207 can comprise a health information portability and applicability act (HIPAA) service 207A, an enterprise service 207B, a basic service 207C, any other digital conference service, or any combination thereof.

The HIPAA service 207A can be a digital conference service 207 that provides any of a high level of security (such as end-to-end encryption), enhanced or high resolution video and/or audio quality, any other HIPAA requirement (such as published by a governmental entity), any other requirement that meets the digital conference configuration associated with the HIPAA service 207A, or any combination thereof. The enterprise service 207B can be a digital conference service 207 that provides any of a high bandwidth, such as a maximum data transfer rate or high speed connection, a high security level, a video and/or audio quality level that satisfies a threshold quality level, unlimited duration, any other requirement that meets the digital conference configuration 206 associated with the enterprise service 207B, or any combination thereof. The basic service 207C can be a digital conference service 207 that provides any of a level of bandwidth, such as a bandwidth efficiency, throughput, quality, or any other requirement that, for example, meets the requirements set forth for a free service (such as limited duration), any other requirement that meets the digital conference configuration 206 associated with the basic service 207C, or any combination thereof. For example, if a user/participant, such as a caller/callee, is a designated medical professional, a professional colleague, or a friend then the associated digital conference configuration 206 can indicate that the HIPAA service 207A is selected for use for the digital conference, the enterprise service 207B is selected for use for the digital conference, or that a basic service 207C is selected for use for the digital conference, respectively.

The digital conference service manager 210 can initiate a digital conference associated with the digital conference service request 212 and establish a digital conference connection based on the digital conference service request 212. The digital conference service manager 210 can send a digital conference service response 213 to the digital conference agent 208 that indicates the status of the digital conference, such as failure/success of the digital conference connection, a bandwidth indicator, a throughput indicator, a quality indicator, a speed indicator, any other indicator for the digital conference connection, the digital conference service 207, or both, or any combination thereof. In one or more embodiments, the digital conference service 207 utilizes a user interface 114, a user interface device 170, an output device 102, an external device, element or component, or any combination thereof to provide and/or receive a video, an audio, a text, or any combination thereof.

In one or more embodiments, the policy manager 204, the digital conference agent 208, and the digital conference service manager 210 are distinct elements, the same element, distinct software applications, the same software application, or any combination thereof.

Figure 3:
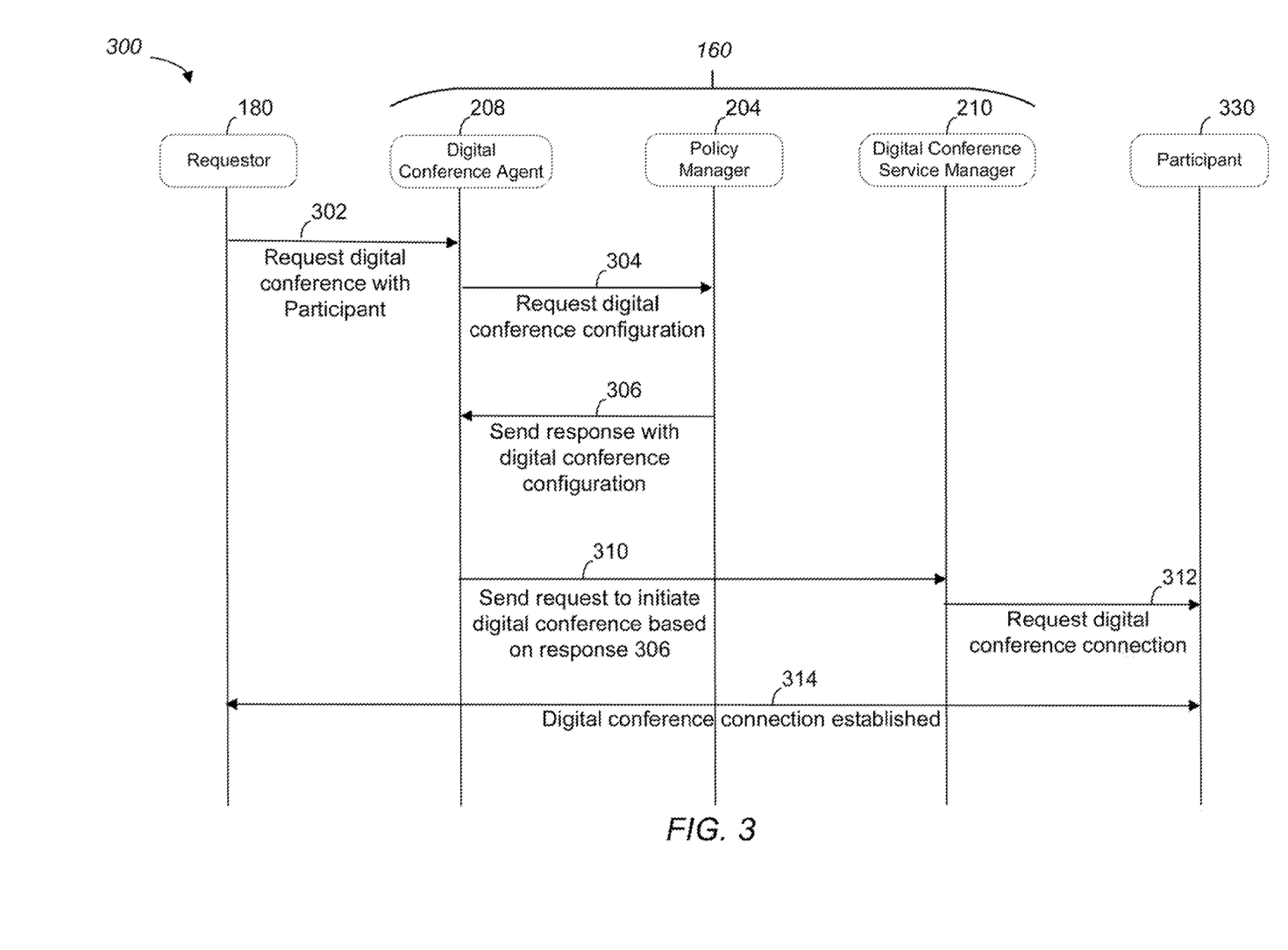
FIG. 3 illustrates an exemplary flow diagram for a digital conference system to establish a digital conference connection, according to one or more aspects of the present disclosure.

FIG. 3 illustrates an exemplary flow diagram for a digital conference system 160 to establish a digital conference connection, according to one or more aspects of the present disclosure. A requestor 180 inputs or sends a request 302 for a digital conference with a participant 330 to the digital conference agent 208 of a digital conference system 160. The participant 330 can be a known person or entity, such as a contact, or digital conference information can be entered via a user interface device 170 that identifies or otherwise provides necessary information to initiate a video conference.

The digital conference agent 208 receives the request or a digital conference request 302 from the requestor 180 and sends a request 304 or a digital conference configuration request for a digital conference configuration 206 to the policy manager 204. The digital conference agent can determine one or more digital conference parameters 140 associated with the request 302 based on one or more network parameters, an identifier associated with a user 180, an identifier associated with the intended recipient of the digital conference (for example, a participant), any other information in the request, or any combination thereof. The request 304 can comprise one or more digital conference parameters 140. The policy manager 204 determines a digital conference configuration 206 based on the digital conference parameters 140 and sends a response 306 to the digital conference agent 208 that comprises the digital conference configuration 206. For example, the policy manager 204 can send to the digital conference agent 208 a digital conference service 207 or an identifier indicative of the digital conference service 207 that was selected by the policy manager 204. The digital conference agent 208 can send a request 310 for the digital conference service manager 210 to initiate a digital conference with the participant 330 based on the request 306, for example, the digital conference service 207 or the identifier indicative of the digital conference service 207 selected by the policy manager 204. The digital conference service manager 210 can send a request 312 to the participant, such as a device associated with the participant 330 and indicated by the one or more digital conference parameters 140, requesting a digital conference using the identified or selected digital conference service 207. If the request 312 is accepted a video conference connection 314 is established between the requestor 180 and the participant 330.

In this way, a digital conference service 207 can be automatically selected from a plurality of digital conference services 207 based on one or more digital conference parameters 140 that provide the requirements, features, or setting for a digital conference between a requestor or user 180 and a participant 330 so that the requestor/user and/or the participant have an improved digital conference experience customized or tailored to the particular needs of the network, a user (such as a host and/or participant), a type of digital conference, or any combination thereof.

Figure 4:
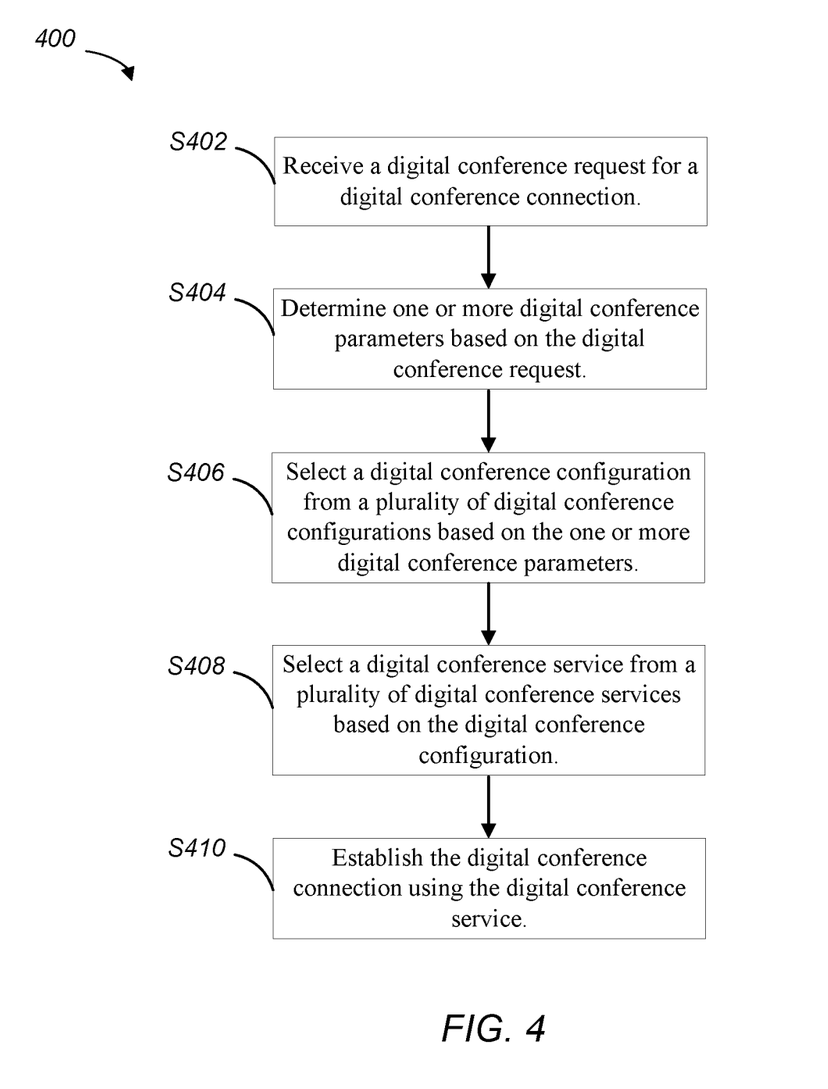
FIG. 4 illustrates a flow diagram for providing one or more commands to a network resource from a control device, according to one or more aspects of the present disclosure.

FIG. 4 illustrates an exemplary flow diagram 400 to establish a digital conference connection. In FIG. 4, it is assumed that any one or more of the devices include their respective controllers and their respective software stored in their respective memories, as discussed above in connection with any of FIGS. 1-3, which when executed by their respective controllers perform the functions and operations in accordance with the example embodiments of the present disclosure (for example, including performing a configuration of one or more network devices). For example, the digital conference system 160 can comprise an application, module, or element, such as a digital conference manager 202 for establishing a digital conference connection. The digital conference manager 202 can comprise one or more computer-readable instructions stored in a memory 110, such as a digital conference solution 112. The one or more computer readable instructions when executed by a processor or controller 108 of the digital conference system 160 can perform any of the steps S402-S410. While the steps S402-S410 are presented in a certain order, the present disclosure contemplates that any one or more steps can be performed simultaneously, substantially simultaneously, repeatedly, in any order or not at all (omitted).

At step S402, a digital conference manager 202, for example, of a digital conference system 160, can receive a digital conference request for a digital conference connection. For example, a patient (a user or caller) can request a digital conference with a physician (a participant or callee) by inputting a user input via a user interface device 170. The user interface device 170 can send the user input to a digital conference agent 208 of the digital conference manager 202 via the user interface 114.

At step S404, the digital conference manager 202 can determine one or more digital conference parameters 140 based on the digital conference request. For example, the digital conference agent 208 can determine one or more digital conference parameters 140 associated with the digital conference request. The determination can be based on the user input (for example, the user input can comprise a user identifier and/or a participant identifier, a particular user (such as user 180 or the intended recipient of the digital conference), the digital conference system 160, a digital conference configuration 206, a digital conference service 207, any other digital conference parameter 140, or any combination thereof.

At step S406, the digital conference manager 202 can select a digital conference configuration from a plurality of digital conference configurations based on the one or more digital conference parameters. For example, the digital conference agent 208 can request a digital conference configuration 206 from a policy manager 204. The policy manager 204 an comprise a plurality of digital conference configurations 206. The policy manager 204 can select one or more digital conference configurations 206 that meet one or more requirements based on the one or more digital conference parameters, for example, one or more threshold requirements that correspond to any one or more of the one or more digital conference parameters. The policy manager 204 can then send the selected one or more digital conference configurations 206 to the digital conference agent 208.

At step S408, the digital conference manager 202 can select a digital conference service from a plurality of digital conference services based on the digital conference configuration. For example, the digital conference agent 208 can select a digital conference service 207 that corresponds to at least one of the one or more selected digital conference configurations 206 received from the policy manager 204 based on any one or more digital conference configurations received by the digital conference agent 208, one or more digital conference parameters 140, one or more thresholds associated with a digital conference 207, a digital conference configuration 206, a digital conference parameter 140, or any combination thereof (such as based on a comparison of a digital conference configuration 206 to a threshold).

At step S410, the digital conference manager 202 can establish a digital conference connection using the digital conference service. For example, the digital conference agent 208 can send the digital conference service manager 210 a selected digital conference service 207 and any other information necessary to establish the requested digital conference connection, such as an identifier indicative of the digital conference service 207 selected and an intended recipient (for example, a callee such as a physician). The digital conference service manager 210 can initiate a digital conference with the intended recipient using the selected digital conference service 207. The digital conference service manager 210 can send a response to the digital conference agent 208 that indicates a status of the digital conference connection, such as a success or failure status. The digital conference agent can log or otherwise store information associated with the digital conference connection including, but not limited to, any of the selected digital conference service 207, the user input, the one or more digital conference parameters 140, the duration of the digital conference connection, the status received from the digital conference service manager 210, any one or more network parameters or network conditions, or any combination thereof. In this way, the user is provided with an improved digital conference connection that is automatically selected and configured to meet the requirements of a particular digital conference.

According to one or more example embodiments of inventive concepts disclosed herein, there are provided novel solutions for establishing a digital conference connection based on one or more digital conference parameters. The digital conference system that includes digital conference agent provides a significant improvement over traditional systems as the novel digital conference system automatically selects a digital conference service from a plurality of digital conference services based on one or more digital conference parameter without. The user has an improved experience as the digital conference service is selected to fit the needs or requirements of the video conference with requiring the user to have knowledge of the various available or required digital conference services. Thus, a user can simply identify the one or more participants for a digital service conference and the digital conference agent 208 ensure that an appropriate a digital conference connection is established.

Each of the elements of the present invention may be configured by implementing dedicated hardware or a software program on a memory controlling a processor to perform the functions of any of the components or combinations thereof. Any of the components may be implemented as a CPU or other processor reading and executing a software program from a recording medium such as a hard disk or a semiconductor memory, for example. The processes disclosed above constitute examples of algorithms that can be affected by software, applications (apps, or mobile apps), or computer programs. The software, applications, computer programs or algorithms can be stored on a non-transitory computer-readable medium for instructing a computer, such as a processor in an electronic apparatus, to execute the methods or algorithms described herein and shown in the drawing figures. The software and computer programs, which can also be referred to as programs, applications, components, or code, include machine instructions for a programmable processor, and can be implemented in a high-level procedural language, an object-oriented programming language, a functional programming language, a logical programming language, or an assembly language or machine language.

The term "non-transitory computer-readable medium" refers to any computer program product, apparatus or device, such as a magnetic disk, optical disk, solid-state storage device (SSD), memory, and programmable logic devices (PLDs), used to provide machine instructions or data to a programmable data processor, including a computer-readable medium that receives machine instructions as a computer-readable signal. By way of example, a computer-readable medium can comprise DRAM, RAM, ROM, EEPROM, CD-ROM or other optical disk storage, magnetic disk storage or other magnetic storage devices, or any other medium that can be used to carry or store desired computer-readable program code in the form of instructions or data structures and that can be accessed by a general-purpose or special-purpose computer, or a general-purpose or special-purpose processor. Disk or disc, as used herein, includes compact disc (CD), laser disc, optical disc, digital versatile disc (DVD), floppy disk and Blu-ray disc. Combinations of the above are also included within the scope of computer-readable media.

The word "comprise" or a derivative thereof, when used in a claim, is used in a nonexclusive sense that is not intended to exclude the presence of other elements or steps in a claimed structure or method. As used in the description herein and throughout the claims that follow, "a", "an", and "the" includes plural references unless the context clearly dictates otherwise. Also, as used in the description herein and throughout the claims that follow, the meaning of "in" includes "in" and "on" unless the context clearly dictates otherwise. Use of the phrases "capable of," "configured to," or "operable to" in one or more embodiments refers to some apparatus, logic, hardware, and/or element designed in such a way to enable use thereof in a specified manner.

While the principles of the inventive concepts have been described above in connection with specific devices, apparatuses, systems, algorithms, programs and/or methods, it is to be clearly understood that this description is made only by way of example and not as limitation. The above description illustrates various example embodiments along with examples of how aspects of particular embodiments may be implemented and are presented to illustrate the flexibility and advantages of particular embodiments as defined by the following claims, and should not be deemed to be the only embodiments. One of ordinary skill in the art will appreciate that based on the above disclosure and the following claims, other arrangements, embodiments, implementations and equivalents may be employed without departing from the scope hereof as defined by the claims. It is contemplated that the implementation of the components and functions of the present disclosure can be done with any newly arising technology that may replace any of the above-implemented technologies. Accordingly, the specification and figures are to be regarded in an illustrative rather than a restrictive sense, and all such modifications are intended to be included within the scope of the present invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

What we claim is:

1. A digital conference system to establish a digital conference connection, the digital conference system comprising:

a memory storing one or more computer-readable instructions; and a processor configured to execute the one or more computer-readable instructions to perform one or more operations to:

receive a digital conference request for a digital conference connection;

determine one or more digital conference parameters based on the digital conference request;

select a digital conference configuration from a plurality of digital conference configurations based on the one or more digital conference parameters;

select a digital conference service from a plurality of digital conference services based on the digital conference configuration; and establish the digital conference connection using the digital conference service.

2. The digital conference system of claim 1, wherein the plurality of digital conference services comprises a health information portability and applicability act (HIPAA) service, an enterprise service, and a basic service.

3. The digital conference system of claim 1, wherein each of the plurality of digital conference configurations are associated with a user profile, a participant profile, or both.

4. The digital conference system of claim 3, wherein the digital conference configuration is selected based on the user profile, the participant profile, or both.

5. The digital conference system of claim 1, wherein the plurality of digital conference configurations comprise at least one of a network configuration, an entitlement configuration, a contact management configuration, and a quality configuration.

6. The digital conference system of claim 1, wherein the at least one of the plurality of digital conference services comprises a calling software development kit (SDK).

7. The digital conference system of claim 1, wherein the processor is configured to execute the one or more computer-readable instructions to further perform one or more further operations to:

receive a user input from a user interface; and wherein the one or more digital conference parameters comprises the user input.

8. A method for a digital conference manager to establish a digital conference connection, the method comprising:

receiving a digital conference request for a digital conference connection;

determining one or more digital conference parameters based on the digital conference request;

selecting a digital conference configuration from a plurality of digital conference configurations based on the one or more digital conference parameters;

selecting a digital conference service from a plurality of digital conference services based on the digital conference configuration; and establishing the digital conference connection using the digital conference service.

9. The method of claim 8, wherein the plurality of digital conference services comprises a health information portability and applicability act (HIPAA) service, an enterprise service, and a basic service.

10. The method of claim 8, wherein each of the plurality of digital conference configurations are associated with a user profile, a participant profile, or both.

11. The method of claim 10, wherein the digital conference configuration is selected based on the user profile, the participant profile, or both.

12. The method of claim 8, wherein the plurality of digital conference configurations comprise at least one of a network configuration, an entitlement configuration, a contact management configuration, and a quality configuration.

13. The method of claim 8, wherein the at least one of the plurality of digital conference services comprises a calling software development kit (SDK).

14. The method of claim 8, further comprising:

receiving a user input from a user interface; and wherein the one or more digital conference parameters comprises the user input.

15. A non-transitory computer-readable medium of a digital conference system storing one or more computer-readable instructions for establishing a digital conference connection, which when executed by a processor of the control device, cause a digital conference manager of the digital conference system to perform one or more operations comprising:

receiving a digital conference request for a digital conference connection;

determining one or more digital conference parameters based on the digital conference request;

selecting a digital conference configuration from a plurality of digital conference configurations based on the one or more digital conference parameters;

selecting a digital conference service from a plurality of digital conference services based on the digital conference configuration; and establishing the digital conference connection using the digital conference service.

16. The non-transitory computer-readable medium of claim 15, wherein the plurality of digital conference services comprises a health information portability and applicability act (HIPAA) service, an enterprise service, and a basic service.

17. The non-transitory computer-readable medium of claim 15, wherein each of the plurality of digital conference configurations are associated with a user profile, a participant profile, or both.

18. The non-transitory computer-readable medium of claim 17, wherein the digital conference configuration is selected based on the user profile, the participant profile, or both.

19. The non-transitory computer-readable medium of claim 15, wherein the plurality of digital conference configurations comprise at least one of a network configuration, an entitlement configuration, a contact management configuration, and a quality configuration.

20. The non-transitory computer-readable medium of claim 15, wherein the one or more instructions when further executed cause the digital conference system to perform one or more further operations comprising:

receiving a user input from a user interface; and wherein the one or more digital conference parameters comprises the user input.

* * * * *